United States Patent [19]

Roizenblatt

[11] Patent Number: 5,286,261
[45] Date of Patent: Feb. 15, 1994

[54] INFLATABLE BALLOON FOR TREATMENT OF RENTAL DETACHMENTS

[76] Inventor: Jaime Roizenblatt, Av. Angélica, 1045-Conjs. 52, 01227 Sao Paulo SP, Brazil

[21] Appl. No.: 855,635
[22] PCT Filed: Aug. 20, 1991
[86] PCT No.: PCT/BR91/00017
§ 371 Date: Apr. 30, 1992
§ 102(e) Date: Apr. 30, 1992
[87] PCT Pub. No.: WO92/03996
PCT Pub. Date: Mar. 19, 1992

[30] Foreign Application Priority Data
Aug. 30, 1990 [BR] Brazil .............................. P19004310

[51] Int. Cl.$^5$ .......................................... A61M 29/02
[52] U.S. Cl. ..................................... 606/192; 604/96
[58] Field of Search ............. 606/191, 192, 194, 195, 606/107; 604/96

[56] References Cited

U.S. PATENT DOCUMENTS

| | | |
|---|---|---|
| 3,834,394 | 9/1974 | Hunter et al. |
| 4,299,227 | 10/1981 | Lincoff |
| 4,517,979 | 5/1985 | Pecenka |
| 4,545,367 | 10/1985 | Tucci ................. 606/195 |
| 4,638,803 | 1/1987 | Rand .................. 606/195 |
| 4,686,962 | 8/1987 | Haber |

FOREIGN PATENT DOCUMENTS

3640013A1 5/1988 Fed. Rep. of Germany .

OTHER PUBLICATIONS

Parabulbar Balloon to Augment a Failing Buckle; Lincoff, H and Kreissig, I.; Am. Journal of Ophthalmology 92; pp. 647-652, 1981.
Results With A Temporary Balloon Buckle For The Repair Of Retinal Detachments; Lincoff, H. and Kreissig, I.; Am. Journal of Ophthalmology 92; pp. 245-251, 1981.
Expandable Silicone Implants for Scleral Buckling; Huamote, F., Refojo, M. and Banuelos, A.; Arch Ophthalmol; 93: pp. 429-431, 1975.
Diagnostic Uses For A Unsecured Balloon Buckle; Lincoff, H. and Kreissi, I.; Mod. Probl. Ophthalmol; 20: pp. 157-163, 1979.
A Temporary Balloon Buckle For The Treatment of Retinal Detachment; Lincoff, H., Kreissig, I. and Hahn, Y. S.; Opthalmology 86: p. 586, 1979.
Expandable Silicone Implants for Scleral Buckling; I. Intro. of a New Concept; Banuelos, A., Refojo, M. F., Schepens, C. L., Arch Ophth. 89: pp. 500-502, 1972.
Expandable Silicone Implants For Scleral Buckling; II Experiments in Vitro; Arch Ophthalmol 90: pp. 127-130, 1973.
Die Balloon Operation; Eine Verlaufskontrolle; Kreissig, I. and Lincoff, H.; Fortschr Ophthalmol 79: p. 229, 1982.
A Fiberoptic Stylette for Localizing the Balloon Buckle; Lincoff, H.; Stergio, P. Kreissig, I.; Arch Ophthalmol 108:607, 1990.
Additional Indications for a Temporary Balloon Buckle; Lincoff, H. and Kreissig, I.; Trans. Ophthalmol; Soc. U.K.
Expandable Silicone Implants for Scleral Buckling; Huamote, F., Refojo, M. and Banuelos, A.; Arch Ophthalmol; 93: pp. 429-431, 1975.

*Primary Examiner*—Stephen C. Pellegrino
*Assistant Examiner*—William Lewis
*Attorney, Agent, or Firm*—Poms, Smith, Lande & Rose

[57] ABSTRACT

An inflatable balloon (34) for use in the treatment of retinal detachments. The balloon (34) has a hollow elliptic-shaped body (36), a solid base (38), and a solid cylindrical stem (40). The balloon is inserted into Tenon's space by inserting a fine blunt-ended needle (52) longitudinally through the solid base (38) and stem (40) of the balloon (34). The needle (52) is then used to guide the balloon (34) into place. Once the balloon (34) is in place, it is inflated with a sterile solution to create the necessary degree of buckling in the sclera. The needle (52) is then removed, with the stem (40) and base (38) maintaining the solution in the body (36) of the balloon (34), and the cylindrical (40) stem is trimmed to the desired length.

18 Claims, 3 Drawing Sheets

INFLATABLE BALLOON FOR TREATMENT OF RENTAL DETACHMENTS

FIELD OF INVENTION

This invention relates generally to an improved inflatable balloon for use in eye surgery. More specifically, the invention relates to an inflatable balloon for use in the treatment of retinal detachments. The balloon is comprised of a hollow elliptic-shaped body, a solid base, and a solid cylindrical stem. The balloon is inserted into Tenon's space by first inserting a fine blunt-ended needle longitudinally through the solid base and stem of the balloon. The needle is then used to guide the balloon into place. Once the balloon is in place, it is inflated with a sterile solution to create the necessary degree of buckling in the sclera. The needle is then removed and the cylindrical stem is trimmed to the desired length.

BACKGROUND OF INVENTION

Vision is accomplished through a complex process wherein light rays are refracted or bent so as to focus on the retina, which then transmits these signals through the fibers of the optic nerve to the brain. To function properly, the retina must contact the choroid, from which it receives a significant portion of the oxygen and glucose required for its normal nourishment. If the retina is detached from the choroid, it is therefore no longer able to accomplish its function.

Retinal detachment is typically the result of subretinal fluid that has permeated between the retina and the choroid through one or more holes in the structure of the retina. The retinal holes generally have the shape of either round holes or "horseshoe" shaped breaks. The permeated subretinal fluid causes portions of the retina to break away from the choroid. As a result of retinal detachment, patients observe some degree of reduction in their visual acuity and field of vision, dependent upon the extend of the retinal detachment.

Treatment of retinal detachment requires occlusion of the ruptures of the retina. In the prior art, occlusion is accomplished by suturing permanent silicone implants to the outer wall of the sclera. The implants cause a buckling or bulging in the sclera toward the area of the retinal holes. The buckling in the sclera causes the sclera and its internally contiguous layer, the choroid, to move inward and occlude the holes of the detached retina. After this occlusion occurs, subretinal fluid is reabsorbed, allowing the retina to settle back into position, in contact with the choroid. In order to induce an inflammatory reaction and augment the adhesiveness of the retina to its normal position in the areas in which it was previously detached, diathermy, cryotherapy, or laser therapy is also applied to the area of the retinal rupture.

This procedure for treating retinal detachment, however, presents several problems. For example, under this procedure, the patient is required to undergo general anesthesia. The surgery also demands a substantial amount of time. Moreover, because the procedure requires extensive surgical manipulation of ocular tissue, the patient is likely to suffer from pain and ocular edema in the post-operative period. Furthermore, substantial dexterity is needed in order to suture the solid implant to the patient's sclera.

Attempts to solve these problems have resulted in Lincoff's inflatable balloon. Prior Art FIG. 1 shows a representation of the Lincoff balloon during treatment of the detached retina. Lincoff's balloon is used to cause a buckling effect similar to that generated by the previously discussed solid permanent implants.

Referring now to FIG. 1 Prior Art, the prior art Lincoff balloon 12 is shown inserted in Tenon's space 14 near a detached retinal portion 18. In the Lincoff balloon technique, the balloon 12 is first inserted into Tenon's space 14 through an incision 20 in the conjunctiva 22. Once it is in a proper location in Tenon's space 14, the balloon 12 is inflated with a saline solution via a catheter 24. The catheter 24 further includes an intricate valve used to maintain the saline solution in the balloon 12. The balloon 12 is shown in FIG. 1 in a semi-inflated state. As the balloon 12 is further inflated, the sclera 26 buckles, this bulge causing the inner wall 32 of the sclera 26 to push the choroid 28 inward and make it to contact a detached retinal portion 18, specifically the portion where the retina holes are located. After the balloon 12 is inflated to the necessary degree, the catheter 24 is taped to the skin near the patient's eye. Several weeks later, after the detached retinal portion 18 has settled in contact with the choroid 28, the balloon 12 and catheter 24 are removed from the patient's eye.

Lincoff's balloon has many advantages over the solid permanent implants. For one, the surgery only requires local anesthesia and surgical time is reduced. Secondly, during the operation, the size of the buckle effect is easily graduated depending on the volume of liquid injected inside the balloon. Also, less tissue manipulation is necessary to insert the balloon, and it is not normally necessary to suture the balloon to the sclera. Finally, diplopia and muscle imbalance does not occur after balloon removal.

The Lincoff balloon, however, also presents several problems. Primarily, the Lincoff balloon is inflated by a catheter which requires an intricate valve to maintain the saline solution in the balloon. After the balloon is inserted and inflated in the Tenon's space of the patient's eye, the catheter protrudes from the patient's eye, disturbing normal eyelid movements and possibly causing corneal erosions. Moreover, the catheter is taped to the patient's skin during the several weeks following the procedure, which adds to the patient's inconvenience and annoyance.

Therefore, a need exists for an inflatable balloon for use in retinal detachment surgery that does not require a catheter and valve as integral components of the balloon.

SUMMARY OF THE INVENTION

One object of the present invention is to provide a balloon for treatment of retinal detachments that does not require a catheter and valve as integral components of the balloon.

Another object of the present invention is to provide an inflatable balloon for treatment of retinal detachments in which the amount and degree of retinal buckling is easily controlled during surgery.

A still further object of the invention is to provide an inflatable balloon for treatment of retinal detachments that does not require the patient to undergo general anesthesia.

Another object of the invention is to provide an inflatable balloon for the treatment of retinal detachments in which overall surgery time is minimized.

These and other objects of the present invention are achieved by an inflatable balloon having a substantially hollow elliptic-shaped body, a solid base, and a solid cylindrical stem. The balloon is inserted into Tenon's space, near the detached retinal portion where the retinal holes are located, by first inserting a fine, blunt-ended needle longitudinally through the stem and base of the balloon and subsequently using the needle to guide the balloon into place. The balloon is then inflated with a sterile solution in order to achieve the desired amount of buckling in the sclera. The needle is next removed from the balloon, with the balloon remaining liquid-tight, and the cylindrical stem is trimmed to the appropriate length. After several weeks, the balloon is removed, with the patient under topical anesthesia, by puncturing the balloon from the conjunctiva, and allowing the liquid to be aspirated by a syringe. The balloon is then easily removable from Tenon's space.

These and other objects of the present invention will now become apparent from the review of the drawings and the following description of the preferred embodiments.

DETAILED DESCRIPTION

Figure 1:
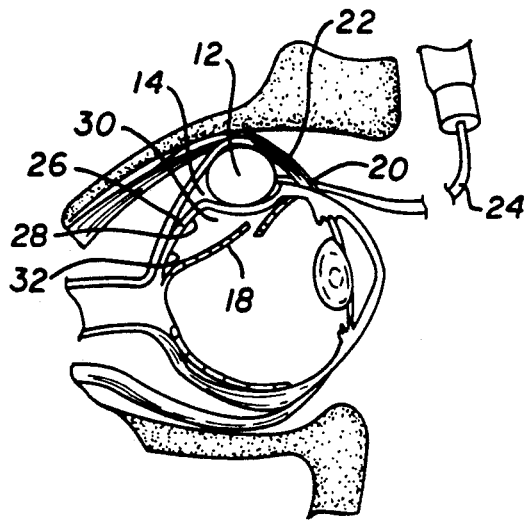
FIG. 1 (Prior Art) is a representation of the prior art Lincoff balloon inserted in Tenon's space near a retinal rupture.
Figure 2:
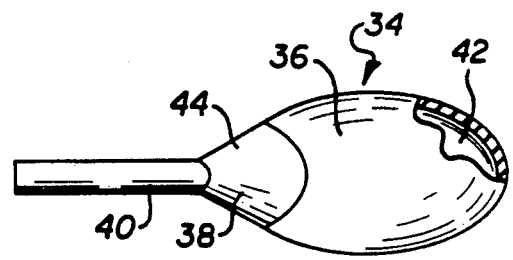
FIG. 2 is a side view, partially broken and partially in cross section, of the first embodiment of the inflatable balloon of the present invention.

Referring now to FIG. 2, a first embodiment of an inflatable balloon 34 of the present invention is shown. The balloon 34 has a substantially hollow ellipse-shaped body 36, a solid base portion 38, and a solid cylindrical stem 40. The ellipse-shaped body 36 further defines a first apex 42 and a second apex 44. The solid base portion 38 is formed integrally in the second. apex 44 of the ellipse-shaped body 36. The cylindrical stem 40 is continuous to the base 38.

The balloon 34 is constructed of a biocompatible material. By way of example, but not of limitation, the balloon 34 may be constructed of a silicone material, a coated latex material, or a polyurethane material.

Figure 3:
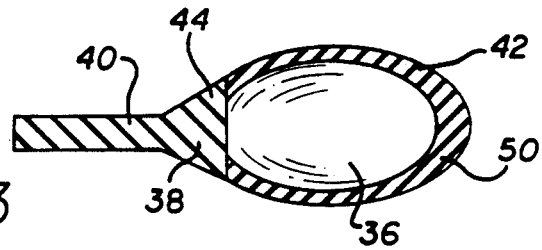
FIG. 3 is a cross sectional side view, of the first embodiment of the inflatable balloon of the present invention with a reinforced apex.
Figure 4:
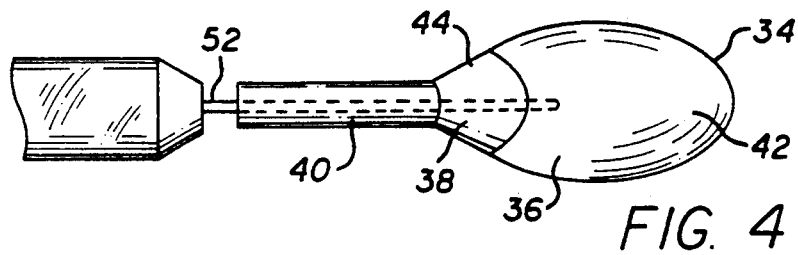
FIG. 4 is a side view of the first embodiment of the inflatable balloon of the present invention with a needle inserted longitudinally through the solid stem and solid base, and into the hollow body of the balloon.

FIG. 3 shows an alternative embodiment of the inflatable balloon 34 of the present invention. In this embodiment, the first apex 42 of the ellipse-shaped body 36 has a reinforced tip 50. The reinforced tip 50 prevents damage to the balloon 34 during insertion and placement of the balloon 34 into Tenon's space 14 in the eye.

In order to begin treatment of the retinal detachments using the balloon 34 of the present invention, a small conjunctival incision 20, for example, three to four millimeters in length, is made at the meridian where the holes of the detached retinal portion 18 are located. Blunt dissection is used to create a narrow path between the sclera 26 and Tenon 27 in the selected meridian.

A fine, blunt-tipped needle 52 is inserted longitudinally through the solid cylindrical stem 40 and the solid base 38 of the balloon 34. The needle 52 is then used to guide the body 36 of the balloon 34 into the proper area of the Tenon's space 14 in the eye. The reinforced tip 50 shown in FIG. 3 serves to prevent rupture of the balloon 34 by the needle 52.

After the balloon 34 is properly located in Tenon's space 14, the balloon 34 is inflated with a sterile saline or sterile and atoxic solution. The buckling and bulging in the sclera 26 created by the balloon 34 are observed with an ophthalmoscope to determine whether the buckling is of the required size and in the proper location. The amount of fluid in the balloon 34 is then adjusted in accordance with these observations. Generally, approximately one cubic centimeter of saline solution is necessary to create adequate buckling. However, in its preferred embodiment, the balloon 34 may contain up to four cubic centimeters of solution.

Figure 5:
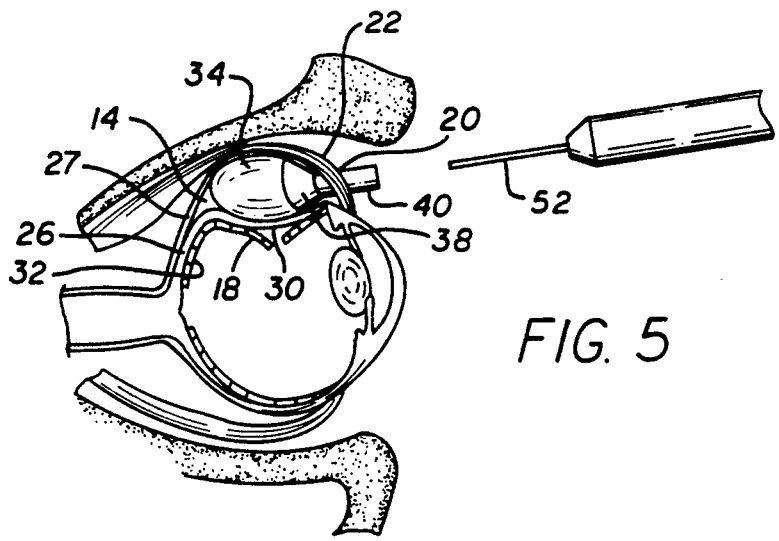
FIG. 5 is a representation of the first embodiment of the inflatable balloon of the present invention inserted in Tenon's space near a retinal rupture.

As shown in FIG. 5, the buckling of the sclera 26, created by the inflated balloon 34, causes the inner wall 32 of the sclera 26 to push the choroid 28 inward and make it to contact a detached retinal portion 18, specifically the portion where the retinal holes are located. After a period of one to two weeks, the detached retinal portion 18 will settle into place, and the subretinal fluid will be reabsorbed.

After the balloon 34 is in the proper location and inflated to the proper degree, the balloon 34 is held steady, and the needle 52 is cautiously removed from the balloon 34. The balloon 34 is preferably held steady during needle removal by grasping the cylindrical stem 40 of the balloon 34 with a pair of forceps. The solid base 38 and stem 40 remain liquid-tight, and prevent the solution from escaping from the body 36 of the balloon 34. After the needle 52 is removed, the stem 40 of the balloon 34 is trimmed down to a desired length. The conjunctival incision 20 is then closed with running sutures.

After a period of one to two weeks, depending on the condition of the patient, the balloon 34 is removed, with the patient under topical anesthesia. For removal purposes, the balloon 34 is punctured from the conjunctiva 20, allowing the liquid to be aspirated from the balloon 34 by means of a syringe. After it is deflated, the balloon 34 is easily slides from Tenon's space 14 with the assistance of a forceps. Preferably, the patient also utilizes antibiotic eye drops when the balloon 34 is in place and for several weeks after removal of the balloon 34.

In addition to the use of the balloon 34, increased adhesion around the retinal holes or breaks of the detached retinal portion 18 is created by one of several methods. For example, prior to the insertion of the balloon 34, cryotherapy may be applied to the sclera 26 in the areas corresponding to the holes or breaks of the detached retinal portion 18. Alternatively, in the postoperative stage, argon laser energy may be applied around the retinal holes or breaks of the area of the detached retinal portion 18 after the retina is flat in position in order to create increased adhesion.

The first balloon is preferably used for retinal detachments caused by a single hole or a group of holes close together that do not subtend more than six to eight mm for about one clock hour at the equator of the eye, or a thirty degree angle area. However, where a group of retinal breaks are spread over an area that subtends an angle larger than thirty degrees or one clock hour area, a second embodiment 60 of the balloon of the present invention is required in order to avoid problems with eye pressure, unnecessary buckling, and excessive orbital compression. The second balloon embodiment 60 enables a surgeon to treat a retinal detachment with breaks spread in an area up to one quadrant in extension, which corresponds to an area subtended by an angle of ninety degrees at the eye equator. This second balloon embodiment 60 is best shown in FIGS. 6 and 7.

Figure 6:
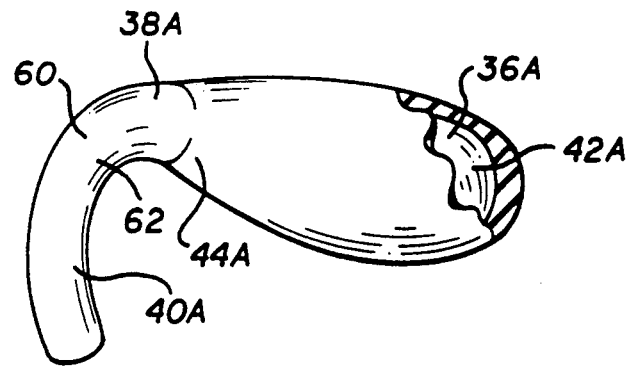
FIG. 6 is a side view, partially broken and partially in cross section, of the second embodiment of the inflatable balloon of the present invention.

Referring now to FIG. 6, the second balloon embodiment 60 is L-shaped, caused by a curvature 62 in the base portion 38a. Therefore, the ellipse-shaped body portion 36a of the balloon 60 extends substantially perpendicular to the stem 40a of the balloon. In comparison to the first embodiment of the balloon, the body portion 36a is narrower and longer than the body portion 36 of the first embodiment.

Figure 8A:
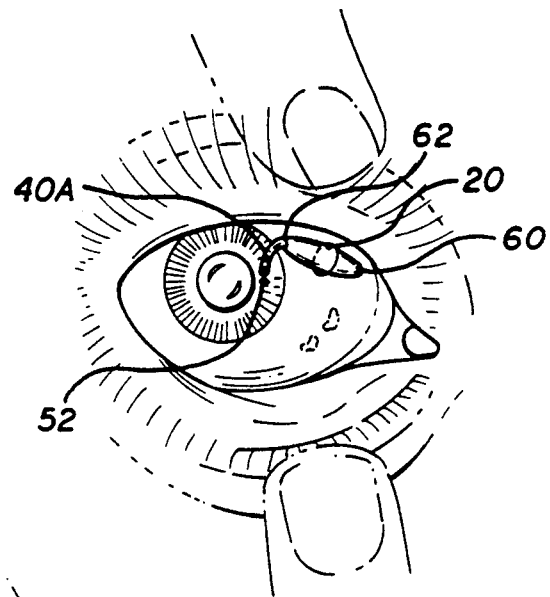
FIGS. 8a, 8b, and 8c are a representation of the insertion technique of the second embodiment of the balloon of the present invention.
Figure 8B:
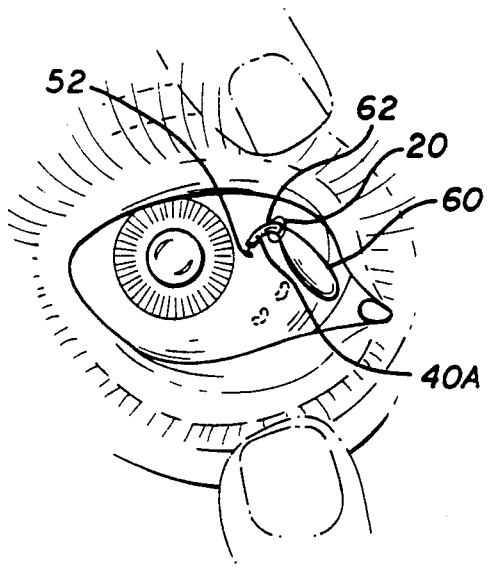
Figure 8C:
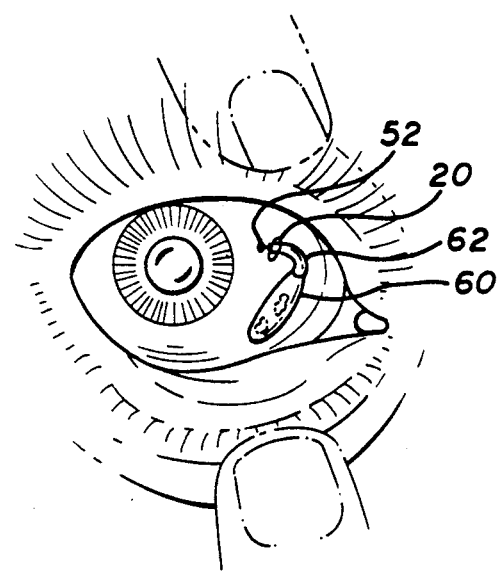

Due to the L-shape of the second balloon embodiment, the insertion technique slightly varies from the insertion of the first embodiment. A representation of the technique of insertion of the balloon is shown in FIG. 8. First, the blunt-tipped needle 52 is longitudinally inserted into the balloon 60 from the base 38a. When the blunt tip of the needle 52 approaches the curvature 62 in the base portion 38a, the curvature 62 is momentarily straightened, creating a temporary straight base portion 38a. The needle 52 is then inserted through the temporarily straightened base portion 38a until the blunt tip of the needle reached the reinforced apex 50a of the ellipse-shaped body 36a. At this point, the needle 52 is bent so as to conform with the original curvature 62 in the base portion 38a.

Figure 7:
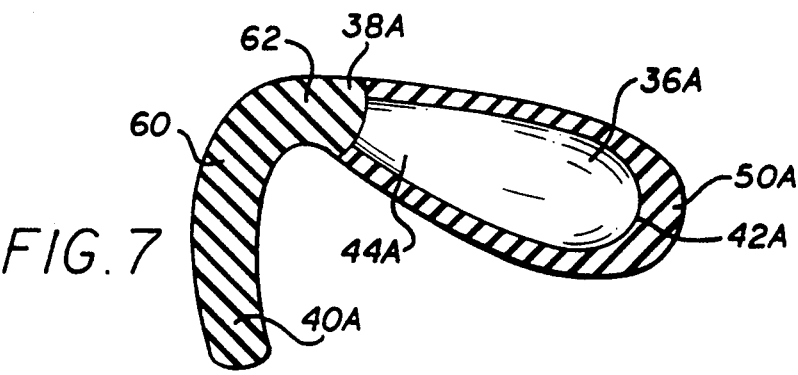
FIG. 7 is a cross sectional side view of the second embodiment of the inflatable balloon of the present invention with a reinforced apex.
Figure 9:
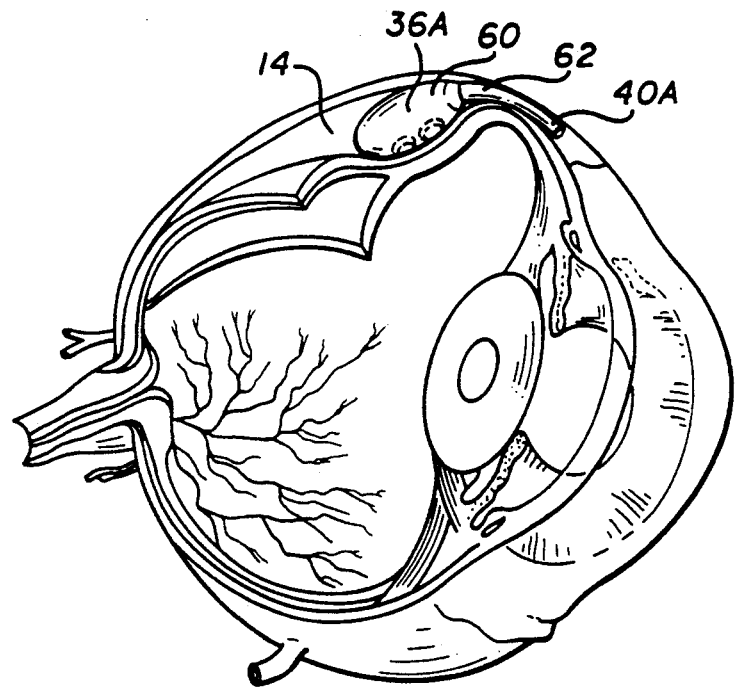
FIG. 9 is a representation of the second embodiment of the inflatable balloon of the present invention inserted in Tenon's space near several "horseshoe" shaped retinal breaks.

Referring, to FIG. 7, in order to insert the balloon 60, a conjunctival incision 20 of two to three millimeters is created in close proximity to the limbus at a meridian different than the meridian where the breaks are located. A spatula is introduced into the opening and used to create a space beneath the conjunctiva and Tenon capsule. The balloon is then introduced into the Tenon's space 14 through the conjunctival incision 20, and directed in a semi-circular movement toward the scleral surface where the retinal breaks are located, and the buckling effect is required.

Generally, the ellipse-shaped body portion 36a will remain in a position parallel to the eye equator, whereas the solid stem 40a and the solid base 38a will remain parallel to one of the eye meridians. When the desired position of the balloon 60 is obtained, the ellipse-shaped body portion 36a is inflated with one milliliter of an atoxic liquid, for example a saline or an antibiotic solution. The balloon of the second embodiment is designed to contain up to four millimeters of solution, but typically, no more than 1.5 millimeters is injected into the balloon. Ophthalmoscopy is then used to observe the position of the buckle effect and to check the circulation of the vessels at the optic papilla. At this point, the physician may make changes in the balloon position and in the volume of solution in the balloon in order to create the desired buckling. If the balloon position is changed, it is preferable to first deflate the balloon.

When all parameters are verified as correct, and the balloon is in the proper position, the physician carefully removes the needle 52 with a semi-circular movement, while simultaneously firmly holding the base portion with a forceps in order to assure that the balloon does not move from the desired position. The balloon of the second embodiment is shown in position in FIG. 8. Then, similar to the insertion of the first balloon embodiment, the solid stem 40a is trimmed to a short piece, so as to not disturb eye movement and normal eyelid closure, and to avoid corneal erosion.

An anterior chamber tap is optionally used to remove a certain amount of liquid or aqueous humor in order to diminish the eye pressure in situations where the circulation is impaired in the vessels of the optic nerve. An alternative to the anterior chamber tap is to administer a hypertonic intravenous solution, for example, isosorbide or Manitol, then monitor the optic nerve circulation ten to fifteen minutes later. The remaining insertion procedure is identical to the insertion procedure of the balloon of the first embodiment as described above.

Having thus described exemplary embodiments of the present invention, it should be noted by those skilled in the art that the within disclosures are exemplary only and that various other alternatives, adaptations and modifications may be made within the scope of the invention. Accordingly, it is to be understood that the present invention is not limited to the precise construction as shown in the drawings and described hereinabove.

I claim:

1. An inflatable balloon for use in the treatment of retinal detachments comprising:
    a substantially hollow elliptic-shaped body, the body having a first apex and a second apex;
    a solid base, the base being integrally formed within the second apex of the body; and
    a solid cylindrical stem formed continuously with the base, wherein the solid base and stem provide a liquid-tight seal for the body of the balloon.

2. An inflatable balloon in accordance with claim 1, wherein the basis formed in a substantially L-shaped configuration, such that elliptic-shaped body is substantially perpendicular to the stem.

3. An inflatable balloon in accordance with claim 1, wherein the balloon, the base, and the cylinder are constructed of a biocompatible material.

4. An inflatable balloon in accordance with claim 3, wherein the biocompatible material is a silicone material.

5. An inflatable balloon in accordance with claim 3, wherein the biocompatible material is a coated latex material.

6. An inflatable balloon in accordance with claim 3, wherein the biocompatible material is a polyurethane material.

7. An inflatable balloon in accordance with claim 1, wherein the first apex of the body is reinforced so as to be thicker than the remaining body.

8. A method of buckling the sclera toward an area of a retinal rupture, using a biocompatible balloon with a solid base portion and solid cylindrical stem, in order to promote an occlusion of the retinal rupture, comprising the steps of;

making a small incision in the conjunctive at the meridian where the rupture is located;

inserting a fine, blunt-tipped needle longitudinally through the solid cylindrical stem and the solid base portion of a substantially hollow inflatable balloon;

using the needle to guide and place the balloon in the desired location of Tenon's space;

inflating the balloon with a sufficient amount of sterile liquid to create the required degree of buckling in the sclera in order to cause the inner wall of the sclera to bulge the choroid and make it to contact the detached retinal portion;

carefully removing the needle from the inflated balloon, thereby sealing the liquid in the balloon;

trimming the cylindrical stem to the desired length;

suturing the incision closed; and removing the balloon from Tenon's space after one to two weeks by puncturing the balloon from the conjunctiva, aspirating the liquid, and sliding the balloon from Tenon's space.

9. A method in accordance with claim 8 wherein the step of inserting the needle through the stem and base portion further includes the steps of:

straightening a curved portion of the base portion with the needle inserted through the base portion;

further inserting the needle until the blunt tip of the needle is in close proximity to the reinforced end of the body of the balloon; and bending the needle and base portion so as to redefine the original curved portion in the base portion.

10. A method in accordance with claim 8 further comprising the steps of:

observing the inside of the eye with an ophthalmoscope after the balloon is partially inflated to determine if the scleral buckling is of an appropriate height and directed to the retinal breaks; and varying the amount of fluid in the balloon in accordance with the observation.

11. A method in accordance with claim 8 further comprising the steps of applying cryotherapy to the sclera in the areas corresponding to the retinal breaks before inserting the balloon in order to provide increased adhesion in the area of the retinal rupture.

12. A method in accordance with claim 8 further comprising the step of applying argon laser energy to the area of the retinal rupture after the retina settles back into position.

13. A device for use in the treatment of retinal detachments comprising:

an inflatable balloon, the balloon being comprised of a substantially hollow elliptic-shaped body having a first apex and a second apex, a solid base integrally formed within the second apex of the body, and a solid cylindrical stem attached to the base, wherein the base and stem provide a liquid-tight seal for the body of the balloon; and removable means releasably attached to the balloon for guiding the balloon into the proper location of Tenon's space in the eye near the detached retinal portion to be treated, the guiding means being detached from the balloon immediately after insertion of the balloon.

14. A device in accordance with claim 13 wherein the removable guiding means is comprised of a fine, blunt-tipped needle, the needle being longitudinally insertable through the stem and base of the balloon, and wherein the base and stem remain liquid-tight after the balloon is guided into position and the needle is removed from the balloon.

15. A device in accordance with claim 14 wherein the balloon further includes a reinforced tip on the first apex of the body in order to prevent balloon damage when the needle is inserted into the balloon.

16. A device in accordance with claim 13 wherein the solid base portion of the inflatable balloon further includes an L-shaped curved portion.

17. A device for use in the treatment of retinal detachments comprising:

an inflatable balloon, the balloon being comprised of a substantially hollow elliptic-shaped body having a first apex and a second apex, a solid base integrally formed within the second apex of the body, and a solid cylindrical stem attached to the base, wherein the base and stem provide a liquid-tight seal for the body of the balloon; and the solid base is formed in a substantially L-shaped configuration, such that the elliptic-shaped body is substantially perpendicular to the stem.

18. A device in accordance with claim 17 further comprising:

removable means releasably attached to the balloon for guiding the balloon into the proper location of Tenon's space in the eye near the detached retinal portion to be treated, guiding means being detached from the balloon immediately after insertion of the balloon; and the removable means comprising a needle being longitudinally insertable through the stem and the base of the balloon, and wherein the base and the stem remain liquid-tight after the balloon is guided into position and the needle is removed from the balloon.

* * * * *

UNITED STATES PATENT AND TRADEMARK OFFICE
CERTIFICATE OF CORRECTION

PATENT NO. : 5,286,261
DATED : February 15, 1994
INVENTOR(S) : Jaime Roizenblatt It is certified that error appears in the above-indentified patent and that said Letters Patent is hereby corrected as shown below:

On the Title page, item [54] line 2, and col. 1, line 2, delete "RENTAL" and insert --RETINAL--.

Signed and Sealed this

Twenty-eighth Day of June, 1994

Attest:

BRUCE LEHMAN

*Attesting Officer*  *Commissioner of Patents and Trademarks*